United States Patent

Onitsuka et al.

[11] Patent Number: 5,635,461
[45] Date of Patent: Jun. 3, 1997

[54] HAIR TINTING SHAMPOO WHICH CONTAINS A DIRECT DYE AND AN ANIONIC SURFACTANT

[75] Inventors: Satoshi Onitsuka, Darmstadt; Hartmut Möhring, Seeheim-Jugenheim, both of Germany

[73] Assignee: Kao Corporation, Japan

[21] Appl. No.: 608,775

[22] Filed: Feb. 29, 1996

[30] Foreign Application Priority Data

Mar. 18, 1995 [DE] Germany .................... 195 09 981.8

[51] Int. Cl.⁶ ................................................ A61K 7/13
[52] U.S. Cl. ................. 510/126; 8/405; 8/435; 8/904; 8/908
[58] Field of Search ................ 8/405, 435, 904, 8/908; 424/70.1, 70.6; 510/126

[56] References Cited

U.S. PATENT DOCUMENTS

| | | | |
|---|---|---|---|
| 4,603,048 | 7/1986 | Konrad et al. | 424/70 |
| 4,818,440 | 4/1989 | Schäfer et al. | 252/546 |
| 5,422,031 | 6/1995 | Nomura | 8/435 |

FOREIGN PATENT DOCUMENTS

| | | |
|---|---|---|
| 0137178 | 4/1985 | European Pat. Off. . |
| 3140134 | 4/1983 | Germany . |

*Primary Examiner*—Paul Lieberman
*Assistant Examiner*—Caroline L. Dvsheck

[57] ABSTRACT

A hair tinting shampoo in an aqueous medium having good lathering properties, excellent color adsorptive capacity and outstanding skin compatibility contains at least one direct, semi-permanent hair dye and at least one anionic surfactant comprising at least 25% by wt., calculated to the total quantity of the anionic surfactant, of an alkyl amidoether carboxylic acid of the general formula I

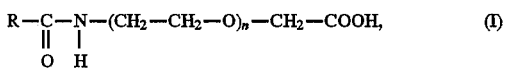

wherein R denotes an alkyl group from 8 to 18 carbon atoms, and n is a number between 1 and 10, and (or) water-soluble salts thereof.

8 Claims, No Drawings

HAIR TINTING SHAMPOO WHICH CONTAINS A DIRECT DYE AND AN ANIONIC SURFACTANT

BACKGROUND OF THE INVENTION

This invention comprises a liquid tinting shampoo in an aqueous medium providing good lathering properties when used with water, rendering the hair soft and pliable and giving it a long lasting lustrous hair color.

According to the invention, this problem is solved by preparing a shampoo in an aqueous medium, which contains at least one direct hair dye and at least one anionic surfactant, characterized in that the anionic surfactant comprises at least 25% by wt., calculated to the total anionic surfactant composition, of an alkyl amidoether carboxylic acid of formula I

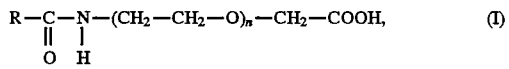

wherein R denotes an alkyl group having 8 to 18 carbon atoms, and n is a number between 1 and 10, and/or the water-soluble salts thereof.

R preferably represents an alkyl group from 12 to 14 carbon atoms, and n is a number from 2.5 to 5, particularly 3 to 4.

The anionic surfactant preferably consists of about 30% to 50% by wt. of the alkyl amidoether carboxylic acid according to formula I. Suitable water-soluble salts thereof are particularly ammonium salts and alkali salts such as the sodium or potassium salt; amine salts, too, are suitable.

So-called tinting shampoos have been known and are on the market since a long time. They normally contain anionic surfactants, particularly alkyl sulfates and alkyl ether sulfates, and at least one direct, i.e. semi-permanent, hair dye in an aqueous medium.

While these shampoos present good lathering properties, the intensity of the hair coloration achieved thereby very often is not satisfactory; and also the skin mildness when using these shampoos is not optimal.

Attempts have been made to overcome these disadvantages by using other anionic surfactants, e.g., sulfosuccinates or polyether carboxylic acids and the water-soluble salts thereof, however, this has not led to optimal coloring results either.

SUMMARY OF THE INVENTION

By using alkyl amidoether carboxylic acids of the kind described above, a shampoo is obtained which presents an optimal result in respect of lathering properties as well as skin mildness and satisfying coloring effect.

A part of the surfactant used herein may comprise customary surface-active substances.

Suitable anionic surfactants besides the alkyl amidoether carboxylic acids are particularly those of the sulfate, sulfonate, carboxylate or alkyl phosphate type generally used in these products, e.g., the well-known $C_{10}$-$C_{18}$-alkyl sulfates, and especially the corresponding ether sulfates, e.g., $C_{12}$-$C_{14}$-alkyl ether sulfates, lauryl ether sulfate particularly having 1 to 4 ethylene oxide groups in the molecule, furthermore monoglyceride sulfates, fatty acid amide sulfates obtained by ethoxylation and subsequent sulfation of fatty acid alkanol-amides, and the alkali salts thereof as well as the salts of long-chain mono- and dialkyl phosphates which are gentle and skin-compatible detergents.

Other suitable anionic surfactants within the scope of the invention are α-olefin sulfonates or the salts thereof and particularly also alkali salts of sulfosuccinic acid semiesters, e.g. the disodium salt of monooctyl sulfosuccinate and alkali salts of long-chain monoalkyl ethoxysulfosuccinates, e.g., disodium lauryl ether sulfosuccinate, which are particularly preferred within the scope of the invention.

It is also advisable to use mixtures of several anionic surfactants, e.g., a mixture of an α-olefin sulfonate and a sulfosuccinate, preferably in a ratio of 1:3 to 3:1.

Protein/fatty acid condensation products of basically known structure, particularly in a proportion between about 0.5% and 5%, preferably 1% to 3% by wt. of the total liquid tinting shampoo composition are also suitable in admixture with other anionic surfactants.

Suitable carboxylates are preferably polyalkyl ether carboxylic acids and the salts thereof of the formula

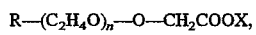

wherein R denotes a $C_8$-$C_{20}$-alkyl group, preferably a $C_{12}$-$C_{14}$-alkyl group, n is a number from 1 to 20, preferably 4 to 17, and X is H or preferably a cation selected from the group of sodium, potassium, magnesium and ammonium, which is optionally substituted by an alkyl or hydroxyalkyl group having a proportion of about 0.1% to about 5%, particularly 0.5% to 3% by wt., calculated to the total tinting shampoo composition.

These products have been known for some time and are sold on the market, e.g., under the trade name "AKYPO-SOFT®".

A survey of anionic surfactants used in liquid tinting shampoos is listed in the monography of K.Schrader, "Grundlagen und Rezepturen der Kosmetika", 2nd Ed., (1989, Hüthig Buchverlag Heidelberg), pp. 683 to 691.

The preferred total quantity of anionic surfactants in liquid tinting shampoos according to the invention is between 0.5% and 25% by wt., especially 2.5% to 15% by wt., particularly preferred about 5% to about 10% by wt., calculated to the total composition.

According to another preferred embodiment of the invention, the liquid tinting shampoo additionally contains about 1% to about 15% by wt., preferably about 2.5% to about 10% by wt., calculated to the total composition, of at least one nonionic surfactant.

A preferred nonionic surfactant belongs to the class of alkyl polyglucosides of the general formula

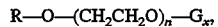

wherein R denotes an alkyl group with 8 to 18 carbon atoms, G is a sugar residue with 5 to 6 carbon atoms, n is a number from 0 to 10, and x is a number between 1.2 and 2.5.

These alkyl polyglucosides have become known recently because of their particular skin mildness and excellent foaming power in liquid shampoos and body cleansing compositions.

Other suitable nonionic surfactants are long-chain fatty acid mono- and dialkanolamides such as coconut fatty acid mono-ethanolamide and myristic fatty acid monoethanolamide which may also be used as foam boosters, as well as the various sorbitan esters such as polyethyleneglycol sorbitan stearic acid ester, fatty acid polyglycol ester or also co-condensates of ethylene oxide and propylene oxide as they are, e.g., on the market under the trade name "Pluronics".

$C_8$-$C_{18}$-fatty alcohol ethoxylates, e.g. those having 10 to 20 ethylene oxide groups per molecule, and ethoxylated $C_8$-$C_{18}$-fatty acid monoalkanolamides having 1 to 20 ethylene oxide groups per molecule may also be used.

Mixtures of anionic surfactants with alkyl polyglucosides which are the preferred nonionic surfactants according to the invention as well as their use in liquid shampoos are known per se, e.g. from European Patent No. 70,074.

The alkyl polyglucosides disclosed therein are basically also suitable within the scope of this invention, as well as the mixtures of sulfosuccinates and alkyl polyglucosides described in European Patent Application No. 358,216.

Surface-active amine oxides may also be used additionally, e.g., in a proportion of about 0.25% to about 5%, preferably about 0.5% to about 3.5% by wt., calculated to the total composition.

Such amine oxides have been known in the art since a long time, e.g., $C_{12}$-$C_{18}$-alkyl dimethyl amine oxides such as lauryl dimethyl amine oxide, $C_{12}$-$C_{18}$-alkyl amidopropyl or -ethyl amine oxides, $C_{12}$-$C_{18}$-alkyl di-(hydroxyethyl) or -(hydroxypropyl) amine oxides, or also amine oxides having ethylene oxide and (or) propylene oxide groups in the alkyl chain.

The compositions according to the invention may also comprise amphoteric surfactants in a proportion of about 0.1% to about 5%, preferably about 0.5% to about 3% by wt., calculated to the total composition. As such, the various known betaines, e.g., fatty acid amidoalkyl betaines, and sulfobetaines, for instance lauryl hydroxy sulfobetaine, are mentioned; long-chain alkyl amino acids have also proved suitable.

In detail betaines of the structure $$R-\overset{\overset{\displaystyle CH_3}{|}}{\underset{\underset{\displaystyle CH_3}{|}}{N^\oplus}}-(CH_2)_n-COO^\ominus \text{ and}$$

$$R-\overset{\overset{\displaystyle}{\|}}{\underset{\underset{\displaystyle O}{}}{C}}-\overset{\overset{\displaystyle}{|}}{\underset{\underset{\displaystyle H}{}}{N}}-CH_2-CH_2-\overset{\overset{\displaystyle CH_2-CH_2-OH}{|}}{\underset{\underset{\displaystyle H}{|}}{N^\oplus}}-CH_2COO^\ominus,$$

wherein R denotes a $C_8$-$C_{18}$-alkyl group and n is 1 to 3, sulfobetaines of the structure $$R-\overset{\overset{\displaystyle CH_3}{|}}{\underset{\underset{\displaystyle CH_3}{|}}{N^\oplus}}-(CH_2)_n-SO_3^\ominus,$$

wherein R denotes a $C_8$-$C_{18}$-alkyl group and n is 1 to 3, and amidoalkyl betaines of the structure $$R-\overset{\overset{\displaystyle}{\|}}{\underset{\underset{\displaystyle O}{}}{C}}-\overset{\overset{\displaystyle}{|}}{\underset{\underset{\displaystyle H}{}}{N}}-(CH_2)_n-\overset{\overset{\displaystyle CH_3}{|}}{\underset{\underset{\displaystyle CH_3}{|}}{N^\oplus}}-CH_2-COO^\ominus,$$

wherein R denotes a $C_8$-$C_{18}$-alkyl group and n is 1 to 3, as well as long-chain alkyl aminocarboxylic acids, may be used.

The liquid tinting shampoos according to the invention may, as a matter of course, comprise all ingredients normally used in these preparations.

Examples for such additives are complexing agents, dyestuffs, preservatives, pH-regulants, Viscosity controllers such as inorganic salts unless they are already directly included in the basic surfactant mixtures, fragrances, pearl gloss agents, thickeners, humectants, vegetable and animal oils such as jojoba oil, etc.

A list of these additives may also be found in Schrader, l.c., pp. 695–722.

Particularly suitable additives for shampoos are hair conditioning compounds. Especially cationic polymers are used for this purpose, preferably in a proportion between 0.1% and 2%, particularly from 0.25% to 1.25% by wt. of the total composition.

European Patent Application No. 337,354 describes the use of cationic polymers together with alkyl polyglucoside surfactants; the cationic polymers listed therein on pp.3 to 7 are also suitable as conditioning additives in the compositions according to the invention.

Further conditioning additives are the well-known protein hydrolyzates, e.g., in a quantity of 0.25% to 5% by wt., preferably 0.5% to 2.5% by wt. of the total composition.

Other suitable conditioning additives are water-soluble collagen or water-soluble collagen derivatives.

Direct dyes are basically well-known. Their type and quantity depends on the coloration desired; normally a proportion between 0.01% and 2.5%, particularly about 0.05% to 1% by wt. is used, whereby cationic dyestuffs are preferred.

Suitable dyestuffs are, e.g., Basic Brown 17, C.I.(Colour Index)-No.12,251; Basic Brown 16, C.I.-No.12,250; Basic Red 1, C.I.-No.45,160; Basic Red 76, C.I.-No.12,245; Basic Yellow 2, C.I.-No.41,000; Basic Yellow 57, C.I.-No.12,719; Basic Blue 7, C.I.-No.42,595; Basic Blue 8, C.I.-No.42,563; Basic Blue 99, C.I.-No.56,059; Basic Violet 1, C.I.-No.42,535; Basic Violet 3, C.I.-No.42,555; Basic Violet 10, C.I.-No.45,170; Basic Green 4, C.I.-No.42,000; Acid Yellow 1, C.I.-No.10,316; Acid Yellow 9, C.I.-No.13,015; Disperse Yellow 3, C.I.-No.11,855; Disperse Yellow 1, C.I.-No.10,345; and Solvent Black 5, C.I.-No.50,415, although this list is by no means comprehensive.

A list of direct hair dyes can also be found in Schrader, l.c., pp. 800–805.

Of course, natural direct dyestuffs, such as henna, camomile, madder root, sandalwood or walnut, may be used additionally. The (optionally) additional employment of optical brighteners, such as Fluorescent Brightener 140, is also possible to achieve light hair colors.

DETAILED DESCRIPTION OF THE INVENTION

The following examples illustrate the invention in detail.

The preparation of the compositions according to the invention is effected by mixing the individual components in water, whereby premixes of the different compounds may also be used.

EXAMPLE 1

| | |
|---|---|
| Coconut amido polyether carboxylic acid (6 EO units), sodium salt | 10.00 (% by wt.) |
| Decyl polyglucoside (P.D.: ≈1.5) | 5.00 |
| Coconut amidopropyl betaine | 3.00 |
| Lauryl hydroxysultaine | 1.50 |
| PEG-10-sorbitan tristearate | 1.00 |
| PEG-60-hydrogenated castor oil | 1.00 |
| EDTA | 0.50 |
| Basic Brown 17 | 0.08 |
| Basic Red 76 | 0.01 |
| Basic Yellow 57 | 0.01 |
| Perfume, preservatives | q.s. |
| Water | @ 100.00 |

After application of this shampoo, which had good lathering properties, an intense, permanent and lustrous brown hair color was achieved.

There was no irritation to the skin.

EXAMPLE 2

| | |
|---|---|
| Coconut amidopolyether carboxylic acid (3–4 EO units), sodium salt | 7.00 (% by wt.) |
| Sodium lauryl ether sulfate | 7.00 |
| Polysorbate 20 | 1.00 |
| Dimethyl lauryl amine oxide | 2.00 |
| Pearl gloss agents (Euperlan ® PK 900) | 2.00 |
| PEG-4-rapeseed monoethanolamide | 3.00 |
| Dimethicone copolyol | 1.00 |
| Cationic cellulose derivative (Polymer ® JR 400) | 0.50 |
| Basic Brown 17 | 0.001 |
| Basic Yellow 57 | 0.01 |
| C.I. Fluorescent Brightener 140 | 0.08 |
| Perfume, preservatives | q.s. |
| Water | @ 100.00 |

After application of this well-foaming shampoo a lustrous light blonde hair color was achieved.

There was no irritation to skin or mucous membranes.

EXAMPLE 3

| | |
|---|---|
| Coconut amidopolyether carboxylic acid (3–4 EO units), sodium salt | 6.00 (% by wt.) |
| Disodium lauryl ether sulfo-succinate | 4.00 |
| Dimethyl lauryl amine oxide | 3.00 |
| Lauryl polyglucoside (P.D.: ≈1.5) | 2.00 |
| PEG-18-glyceryl oleate/cocoate | 2.00 |
| Lauryl hydroxysultaine | 1.00 |
| PEG-15-glyceryl isostearate | 1.00 |
| Solubilizer (Trideceth-8) | 1.00 |
| Sucrose laurate | 0.50 |
| Polyquaternium-7 | 0.50 |
| Basic Red 76 | 0.08 |
| Basic Yellow 57 | 0.01 |
| Basic Blue 99 | 0.01 |
| Henna extract | 0.10 |
| Perfume, preservatives | q.s. |
| Water | @ 100.00 |

This strongly lathering shampoo produced a lustrous red hair color.

There was no irritation to skin or mucous membranes.

EXAMPLE 4

| | |
|---|---|
| Lauryl amidopolyether carboxylic acid (3–4 EO units), sodium salt | 5.00 (% by wt.) |
| Lauroyl sarcosinate, sodium salt | 4.00 |
| Decyl polyglucoside (P.D.: ≈1.5) | 3.00 |
| Coconut amidopropyl betaine | 3.00 |
| PEG-120-methyl glucose dioleate | 2.50 |
| Polyglyceryl caprinate | 1.00 |
| Basic Blue 99 | 0.03 |
| Perfume, preservatives | q.s. |
| Water | @ 100.00 |

Used on grey hair, this composition revitalized the lustre and covered any yellow shade.

There was no irritation to skin or mucous membranes.

The surprising effect of using alkyl amidoether carboxylic acids in tinting shampoos according to the invention, in comparison with known surfactants, is also illustrated by the following comparison tests:

Six different dyestuff solutions in water were prepared containing each 0.1% Basic Red 76 and 2% of an anionic surfactant according to the following table:

| Solution No. | Surfactant |
|---|---|
| 1 | Disodium lauryl ether sulfosuccinate |
| 2 | Polyether carboxylic acid (4,5 EO), sodium salt |
| 3 | Alkyl amidoether carboxylic acid (1 EO), sodium salt |
| 4 | Alkyl amidoether carboxylic acid (2 EO), sodium salt |
| 5 | Alkyl amidoether carboxylic acid (3 EO), sodium salt |
| 6 | Alkyl amidoether carboxylic acid (4 EO), sodium salt |

After 20 minutes processing at 40° C. on hair strands which were rinsed with water subsequently, the ΔE-values for hair lustre were measured by the well-known Minolta CR 200. The results prove the superior effect of the alkyl amidoether carboxylates used by the invention.

| ΔE-Values | |
|---|---|
| Solution No. | ΔE |
| 1 | 22.6 |
| 2 | 48.5 |
| 3 | 56.1 |
| 4 | 58.1 |
| 5 | 58.4 |
| 6 | 58.2 |

What is claimed is:

1. Tinting shampoo comprising about 0.01–2.5 wt % of at least one direct hair dye and about 0.5–2.5 wt % of at least on anionic surfactant in an aqueous medium, wherein the anionic surfactant comprises at least 25% by wt., calculated to the total composition of the anionic surfactant, of at least one of an alkyl amidoether carboxylic acid of formula I

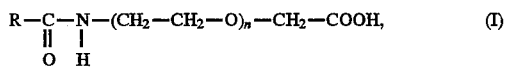

$$R-\underset{\underset{O}{\|}}{C}-\underset{\underset{H}{|}}{N}-(CH_2-CH_2-O)_n-CH_2-COOH, \quad (I)$$

wherein R denotes an alkyl group having 8 to 18 carbon atoms, and n is a number between 1 and 10, and water-soluble salts thereof.

2. Tinting shampoo according to claim 1, wherein R denotes alkyl group having 12 to 14 carbon atoms.

3. Tinting shampoo according to claim 1, wherein n is a number between 2.5 and 5.

4. Tinting shampoo according to claim 3, wherein n is 3 to 4.

5. Tinting shampoo according to claim 1, wherein the anionic surfactant comprises at least 50% by wt. of an alkyl amidoether carboxylic acid of formula I.

6. Tinting shampoo according to claim 1, further comprising at least one of a further anionic, amphoteric and nonionic surfactant.

7. Tinting shampoo according to claim 6, further comprising one of a sulfosuccinate and alkyl ether sulfate as further anionic surfactant.

8. Tinting shampoo according to claim 6, wherein a $C_8$-$C_{12}$-alkyl glucoside having a condensation degree from 1.2 to 2.5 is present as nonionic surfactant.

* * * * *